US012551213B2

(12) United States Patent
Huang et al.

(10) Patent No.: US 12,551,213 B2
(45) Date of Patent: Feb. 17, 2026

(54) SURGICAL DEVICE

(71) Applicant: Astron Medtech Corporation, Wilmington, DE (US)

(72) Inventors: Yi Hsi Huang, Taipei (TW); I-Lin Tsai, Taipei (TW); Kuei-Hua Chen, Taichung (TW)

(73) Assignee: Astron Medtech Corporation

( * ) Notice: Subject to any disclaimer, the term of this patent is extended or adjusted under 35 U.S.C. 154(b) by 224 days.

(21) Appl. No.: 18/493,507

(22) Filed: Oct. 24, 2023

(65) Prior Publication Data

US 2025/0127506 A1 Apr. 24, 2025

(51) Int. Cl.
*A61B 17/04* (2006.01)

(52) U.S. Cl.
CPC ................................ *A61B 17/0469* (2013.01)

(58) Field of Classification Search
CPC .... A61B 2017/2912; A61B 2017/2913; A61B 2017/2919; A61B 2017/292; A61B 2017/2946; A61B 17/0469; A61B 17/0483
See application file for complete search history.

(56) References Cited

U.S. PATENT DOCUMENTS

2013/0204247 A1* 8/2013 Triplett .............. A61B 17/2909
606/53

* cited by examiner

*Primary Examiner* — Todd J Scherbel
(74) *Attorney, Agent, or Firm* — Best & Flanagan LLP

(57) ABSTRACT

A surgical device has a handle, a shaft connecting to the handle, a clamping portion disposed on one end of the shaft different from the end connected to the handle, a hook fixedly connected to the shaft and a closing member pivotally connected to the hook, and a control mechanism mounted on the handle and extending through the shaft and connect to the clamping portion, wherein the control mechanism controls the pivoting of the closing member to switch the clamping portion between a closed position and an opened position.

9 Claims, 7 Drawing Sheets

SURGICAL DEVICE

FIELD OF INVENTION

The present invention relates to a surgical device, especially to a surgical device suitable for minimally invasive surgery.

BACKGROUND OF THE INVENTION

When performing an internal suturing in a conventional way of a surgery, a suturing tool, such as a plier or a tweezer, etc., is inserted into a patient's body through a wound opening in the patient's skin to perform the suturing. As to shorten the recovery period of surgical patients and narrow the size of the wound, a minimally invasive surgery has become increasingly popular. However, the size of the wound for performing the minimally invasive surgery is too small that it is difficult for the suturing tool to insert therein for suturing. Thus, it is urge to develop a surgical device suitable for helping minimally invasive surgery in the related field.

SUMMARY OF THE INVENTION

In order to develop a surgical device suitable for helping minimally invasive surgery, the present invention provides a surgical device, comprising a handle, a shaft connecting to the handle, a clamping portion disposed on an end of the shaft opposite the handle and comprising a hook fixedly connected to the shaft and a closing member pivotally connected to the hook, and a control mechanism disposed on the handle, extending through the shaft and connect to the clamping portion, wherein the control mechanism controls the pivoting of the closing member to switch the clamping portion between a closed position and an opened position.

When using the surgical device in accordance with the present invention, the shaft and the clamping portion of the surgical device may be inserted into a patient's body through a wound opening in the patient's skin, then the hook can hook a suture, which have been previously placed in the patient's body, in the opened position. Thus, the user can perform operations such as suturing, knotting, or extracting at least a portion of the suture from the patient's body by manipulate the handle 10 maintained outside the patient's body.

Then the user pulls the control mechanism to make the closing member be pivoted that the closed space is formed in the clamping portion. The closed space may ensure at least a portion of the suture can be captured between the hook and closing member and also can prevent the hook from hooking and causing damage on tissues or organs when the clamping portion is displaced in the body.

By repeatedly switch the clamping portion between the closed position and the opened position, the user can control the suture by the handle outside the patient's body to perform suturing-related operations of the operation.

DETAILED DESCRIPTION OF THE PREFERRED EMBODIMENTS

In order to make purposes, technical solutions, and advantages of the present invention to be clearer, the following content provides some preferred embodiments in accordance with the present invention.

Figure 1:
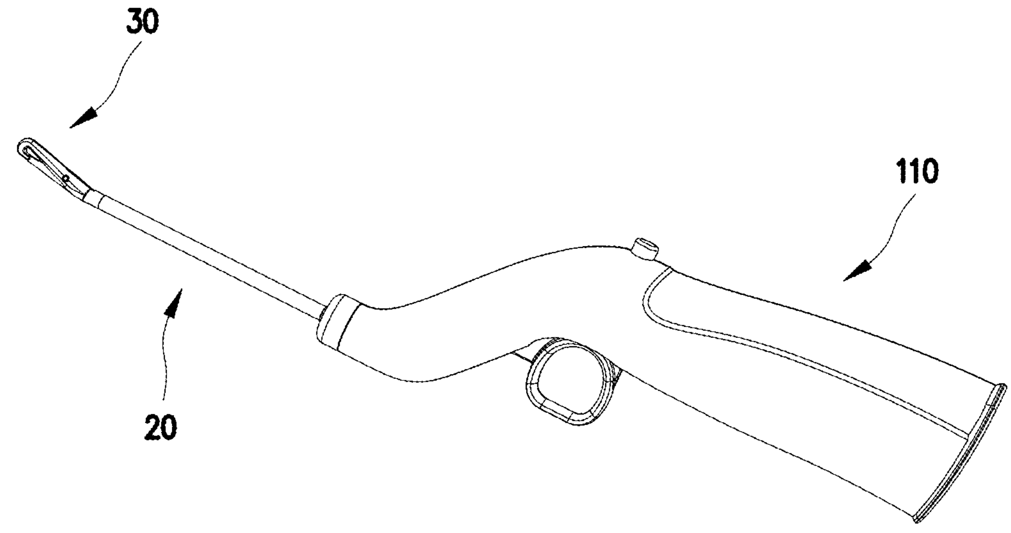
FIG. 1 is a perspective view of a preferred embodiment of a surgical device in accordance with the present invention.
Figure 2:
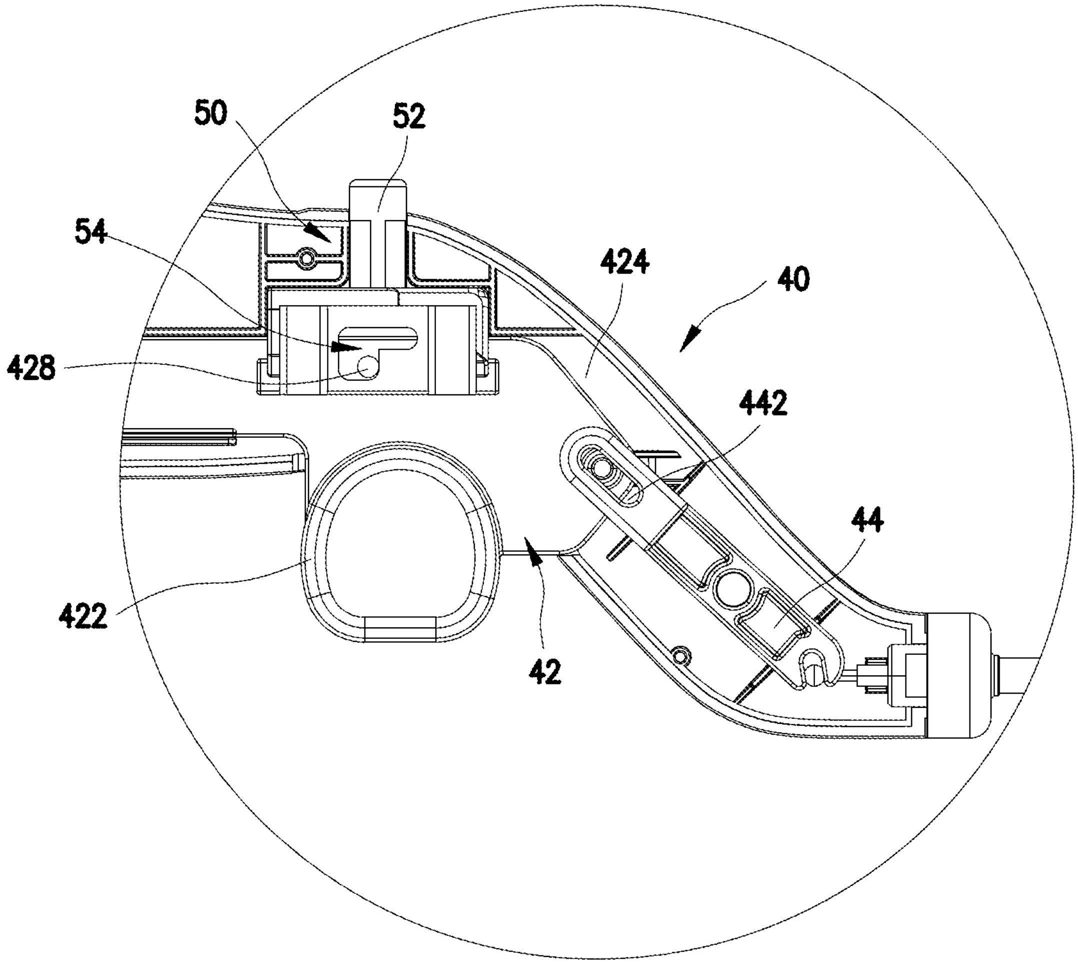
FIG. 2 is an enlarged side view in partial section of the surgical device in FIG. 1.
Figure 3:
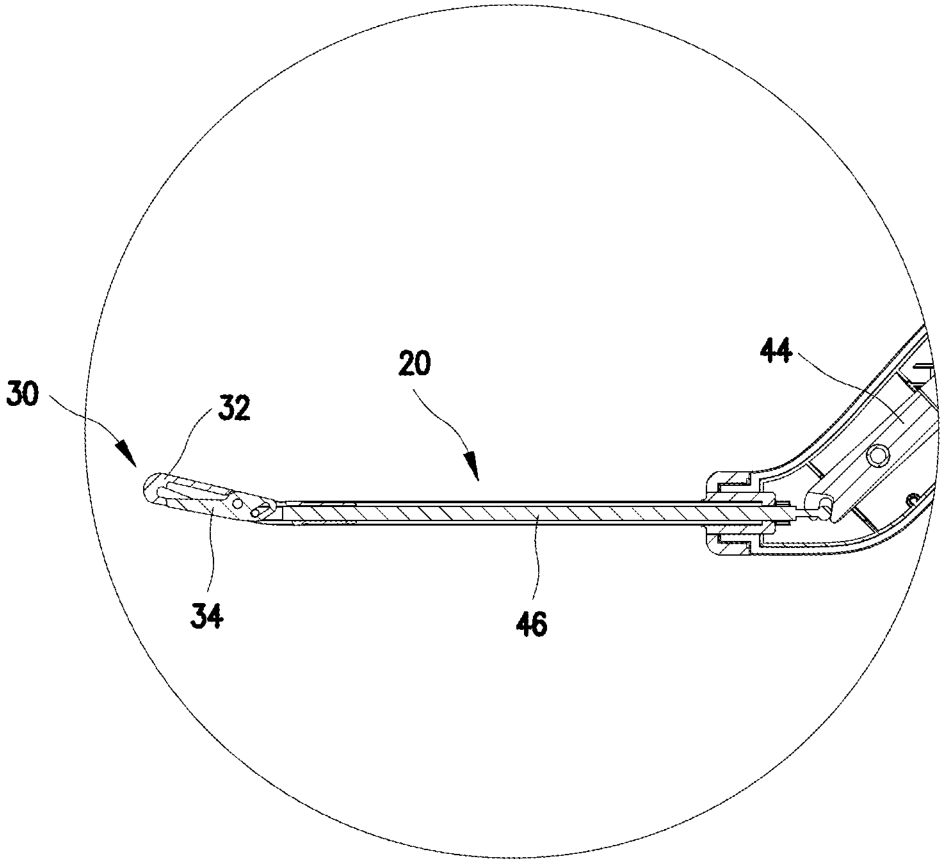
FIG. 3 is another enlarged side view in partial section of the surgical device in FIG. 1.

With reference to FIG. 1 to FIG. 3, a surgical device in accordance with the present invention comprises a handle 10, a shaft 20 and a clamping portion 30. The handle 10 is applied for holding from a user. As shown in figures, the handle 10 can be a hollow one-piece structure or can be composed of two-piece shells. The shaft 20 is connected with the handle 10, and the clamping portion 30 is disposed on an end of the shaft 20 opposite the handle 10. The clamping portion 30 comprises a hook 32 and a closing member 34. The hook 32 is fixedly connected to the shaft 20, and the closing member 34 is pivotally connected to the hook 32. The closing member 34 can open or close the hook 32 by relative pivot to the hook 32, thereby loosening or clamping a suture to perform a surgical suturing.

Figure 4:
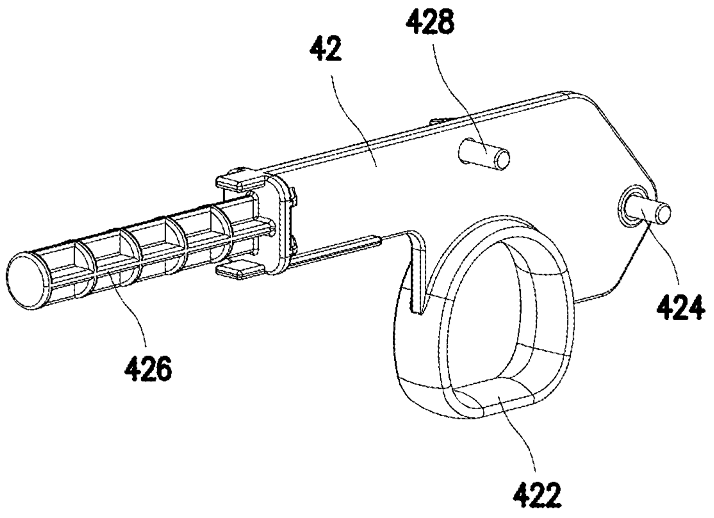
FIG. 4 is an enlarged perspective view of an activator of the surgical device in FIG. 1.

In order to control the pivotal movement of the closing member 34, the present invention further provides a control mechanism 40, referring to FIG. 2 to FIG. 4, the control mechanism 40 is mounted on the handle 10, extends through the shaft 20, and is connected with the clamping portion 30. The control mechanism 40 can control the pivoting of the closing member 34 relative to the hook member 32 to make the hook 32 be switch between a closed position and an opened position. The control mechanism 40 comprises an activator 42, a connector 44 and a linkage shaft 46. The activator 42 is movably installed in the handle 10 and comprises a ring 422 placed on the activator 42 and protruding to the outside of the handle 10, and an activating rod 424 protruding from the activator 42. The connector 44 is movably installed in the handle 10 and is sleeved around the starting shaft 424, and the connector 44 is movable relatively to the starting shaft 424. A slot 442 is defined in an end of the connector 44 adjacent to the activator 42 of, and the activating rod 424 of the activator 42 is movably inserted into the slot 442. The linkage shaft 46 is movably placed in and extends through the shaft 20. One end of the linkage shaft 46 is pivotally connected to an end of the connector 44 opposite the activator 42. The other end of the linkage shaft 46 is pivotally connected to an end of the closing member 34.

Figure 6:
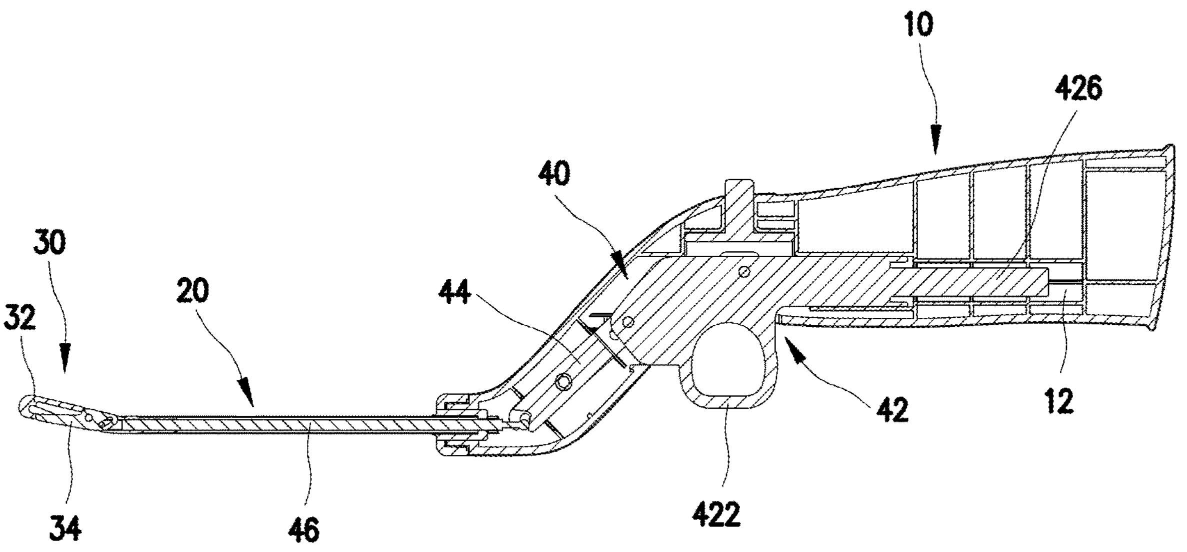
FIG. 6 is an operational cross-sectional side view of a clamping portion with a closed position of the surgical device in FIG. 1.
Figure 7:
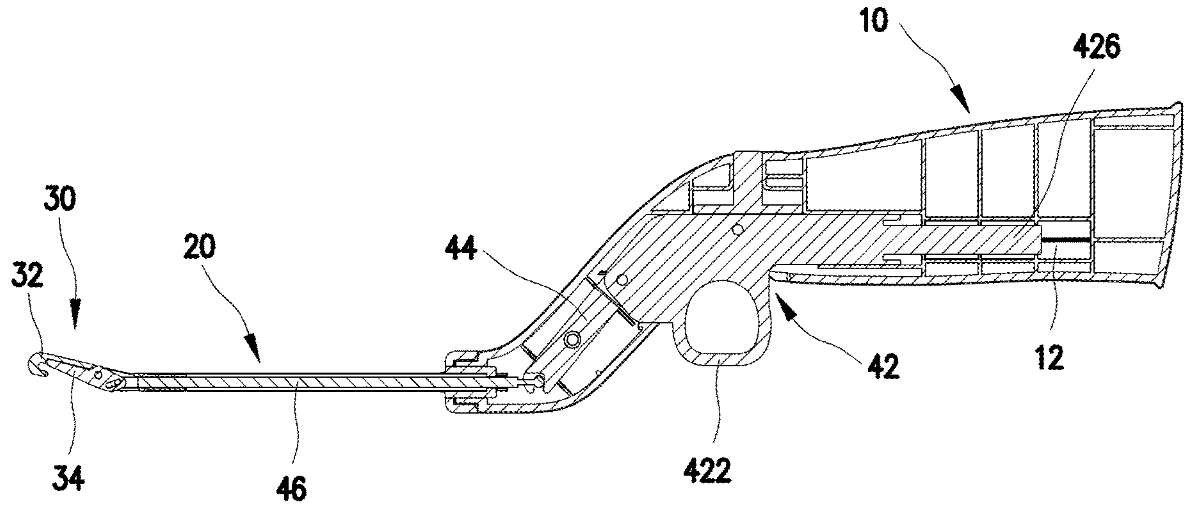
FIG. 7 is an operational cross-sectional side view of the clamping portion with an opened position of the surgical device in FIG. 1.

Thus, when the user hooks the ring 422 with a finger and pulls the ring 422, the activator 42 be moved relative to the handle 10, whereby the activating rod can be moved relative to the slot 442 of the connector 44 then making the connector 44 to rotate. Then the linking shaft 46 is driven to move relative to the shaft 20, and the closing member 34 is pivotally rotated relative to the hook 32 to exhibit the closed position. When the clamping portion 30 is in the closed position, a closed space is formed between the hook 32 and the closing member 34, as shown in FIG. 6. When the activator 42 is moved back, the closing member 34 may be pivoted in an opposite direction due to the movement of the activator 42 and the linkage shaft 46, the space between the hook 32 and the closing member 34 is opened, and the clamping part 30 may be switch into the opened position, as shown in FIG. 7.

When using the surgical device in accordance with the present invention, the shaft 20 and the clamping portion 30 of the surgical device may be inserted into a patient's body through a wound opening in the patient's skin, then the hook 32 can hook a suture, which have been previously placed in the patient's body, in the opened position. Thus, the user can perform operations such as suturing, knotting, or extracting at least a portion of the suture from the patient's body by manipulate the handle 10 maintained outside the patient's body. Then the user pulls the ring 422 to make the closing member 34 be pivoted that the closed space is formed in the clamping portion 30. The closed space may ensure at least a portion of the suture can be captured between the hook 32 and closing member 34 and also can prevent the hook 32 from hooking and causing damage on tissues or organs when the clamping portion 30 is displaced in the body. By repeatedly switch the clamping portion between the closed position and the opened position, the user can control the suture by the handle 10 outside the patient's body to perform suturing-related operations of the operation.

Preferably, in order to make the movement of the activator 42 more smoothly relative to the handle 10, FIG. 4 and FIG. 6 reveals a guiding shaft 426 protruding from the activator 42, and a guiding track 12 formed in the handle 10. The guiding track 12 allows the guiding shaft 426 movably insert therein to guide the activator 42 to move forward or backward smoothly. More preferably, an elastic portion is placed in the handle 10 to urge the activator 42 and provide the activator 42 a bias force. Therefore, the operator may release the ring 422 after pulling, and the activator 42 can automatically return to an original position, before the ring 422 is pulled, via the elastic portion. Then the closing member 34 is pivoted in the opposite direction to open the space between the hook 32 and closing member 34. Moreover, the elastic portion may be a spring.

Figure 5:
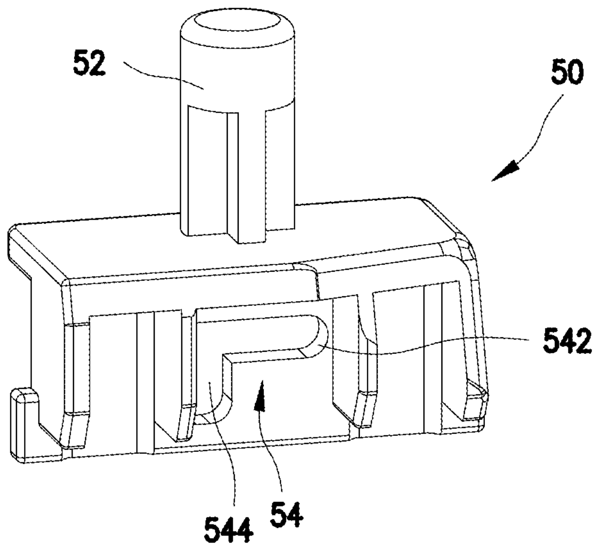
FIG. 5 is an enlarged perspective view of a locking portion of surgical device in FIG. 1.

In some embodiments, referring to FIG. 2, FIG. 4 and FIG. 5, the control mechanism 40 further comprises a locker 50 which is mounted on the handle 10, and the locker 50 can be moved upwardly and downwardly relative to the handle 10. The locker 50 comprises a press button 52 protruding outside the handle 10 from the topside of the locker 50, and a locking hole 54 with an inverted L shape passes through the locker. The inverted L shape defines a horizontal part 542 and a locking part 544 formed at one end of the horizontal part 542. The activator 42 forms a locking rod 428 which extends through the locking hole 54 and is movable in the horizontal part 542. Thus, when the clamping portion 30 is in the opened position, the position of the locking rod 428 can align the locking part 544. Then the locking rod 428 can enter locking part 544 by moving the locker 50 upwardly to hold the opened position and prevent the operator to active (pull) the ring 422, and the clamping portion 30 can be fixed and the hook 322 can be applied to capture the suture. To shift the clamping portion 30 in the closed position, the pressing part 52 is pressed downward and the locking rod 428 can leave the locking part 544 and move to align the horizontal part 542. Meanwhile, the ring 422 is allowed to be pulled by the user, and the closing member is pivoted, the opened position of the clamping portion 30 then completed. In some embodiments, an elastic portion also can be placed in the handle 10 to urge the locker 50, and can provide the locker 50 the bias force while the locking rod 428 enters the locking part 544.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A surgical device, comprising:

a handle;

a shaft connecting to the handle;

a clamping portion disposed on an end of the shaft opposite the handle and comprising a hook fixedly connected to the shaft and a closing member pivotally connected to the hook; and a control mechanism disposed on the handle, extending through the shaft and connected to the clamping portion, wherein the control mechanism controls the pivoting of the closing member to switch the clamping portion between a closed position and an opened position; and the control mechanism comprises:

a locker mounted in the handle, wherein the locker is movable from top to bottom relative to the handle, a press button protrudes outside the handle from the topside of the locker, and a locking hole with an inverted L shape defined through the locker, the inverted L shaped locking hole defines a horizontal part and a locking part formed at one end of the horizontal part; and means for driving the closing member to be pivoted relatively to the hook, comprising a locking rod movably extending through the horizontal part of the locking hole.

2. The surgical device as claimed in claim 1, wherein the handle is hollow and the control mechanism is placed in the handle.

3. The surgical device as claimed in claim 2, wherein the control mechanism comprises an activator, a connector and a linkage shaft, the activator is movably installed in the handle, the connector is movably installed in the handle and is sleeved around the activator, the linkage shaft is movably placed in and extends through the shaft, an end of the linkage shaft opposite the activator is pivotally connected to the connector, an end of the linkage shaft is pivotally connected to one end of the closing member, when the activator is pulled, the connector is rotated, and the linking shaft is driven to move relative to the shaft that make the closing member be pivoted relatively to the hook.

4. The surgical device as claimed in claim 3, wherein a ring is placed on the activator and protrudes outside the handle.

5. The surgical device as claimed in claim 4, wherein an activating rod protrudes from the activator, a slot is defined in one end the connector adjacent to the activator, and the activating rod is movably inserted into the slot.

6. The surgical device as claimed in claim 5, wherein a guiding shaft protrudes from the activator, a guiding track is formed in the handle and the guiding track allows the guiding shaft movably inserted in the guiding track.

7. The surgical device as claimed in claim 4, wherein a guiding shaft protrudes from the activator, a guiding track is formed in the handle and the guiding track allows the guiding shaft movably inserted in the guiding track.

8. The surgical device as claimed in claim 3, wherein a guiding shaft protrudes from the activator, a guiding track is formed in the handle and the guiding track allows the guiding shaft movably inserted in the guiding track.

9. The surgical device as claimed in claim 3, wherein an activating rod protrudes from the activator, a slot is defined in an end of the connector adjacent to the activator, and the activating rod is movably inserted into the slot.

* * * * *